United States Patent
Winkler et al.

(10) Patent No.: US 7,288,515 B1
(45) Date of Patent: *Oct. 30, 2007

(54) METHODS FOR MAKING CLEAR FRAGRANCES AND FORMULATIONS

(75) Inventors: Bernard Erich Winkler, Houston, TX (US); Robert Charles Baker, Houston, TX (US)

(73) Assignee: Infrin, LLC, Houston, TX (US)

( * ) Notice: Subject to any disclaimer, the term of this patent is extended or adjusted under 35 U.S.C. 154(b) by 197 days.

This patent is subject to a terminal disclaimer.

(21) Appl. No.: 10/463,183

(22) Filed: Jun. 17, 2003

(51) Int. Cl.
*A61L 9/04* (2006.01)
*A61K 8/00* (2006.01)

(52) U.S. Cl. .............................. 512/4; 512/1
(58) Field of Classification Search ............ 512/4
See application file for complete search history.

*Primary Examiner*—Jill Warden
*Assistant Examiner*—Neil Turk
(74) *Attorney, Agent, or Firm*—Buskop Law Group, PC; Wendy Buskop

(57) ABSTRACT

Methods of forming clear fragrances and formulations are described herein. The method includes providing a commercial fragrance formulation including a first concentration of a fragrance component and a second concentration of a nonessential component. The method further includes identifying the nonessential component, wherein the nonessential component includes an alcohol, an ester, a hydrocarbon, an aldehyde, a resin, other crystalline aroma chemicals, a first essential oil or combinations thereof, determining the second concentration and removing at least a portion of the nonessential component from the commercial fragrance formulation to form a first formulation, wherein the portion of the nonessential component is from about 5 wt. % to about 95 wt. % of the commercial fragrance formulation. The method further includes adding an essential component to the first formulation to form a second formulation, wherein the essential component is added to the first formulation in an amount substantially equal to the portion of the nonessential component removed from the commercial fragrance formulation. The method can further include preparing a second composition from the second formulation and processing the second composition to form the clear fragrance, wherein the processing comprises mixing, heating to a temperature of from about 20° C. to about 68° C. or combinations thereof, and wherein the clear fragrance is adapted to enhance solubility, enhance functional compatibility, enhance performance, reduce sweating or combination thereof, of the clear fragrance when added to an article.

29 Claims, 1 Drawing Sheet

METHODS FOR MAKING CLEAR FRAGRANCES AND FORMULATIONS

BACKGROUND

1. Field of Invention

Embodiments of the invention relate to methods for making clear fragrances.

2. Description of Related Art

The concentration of conventional clear fragrances added to household articles is generally limited from a variety of factors, such as either the clear fragrance's or the article's solubility or compatibility, for example. Previously encountered problems have also included color problems, e.g., the fragrance is opaque, physical structure problems, performance, such as diffusion of the fragrance from the product and the longevity of the fragrance in the product, and physical appearance problems. Further, a high concentration of fragrance in the household article can provide too much color to the end product.

Therefore, it is desirable to form a clear fragrance that eliminates or minimizes the problems encountered in forming fragranced household articles. Additionally a need exists for methods of producing cheaper articles capable of producing strong fragrances.

SUMMARY

Embodiments of the invention generally include a method of forming a clear fragrance formulation. The method generally includes providing a commercial fragrance formulation including a fragrance component and a an additional component. The method further includes identifying the additional component, wherein the additional component includes an alcohol, an ester, a hydrocarbon, an aldehyde, a resin, other crystalline aroma chemicals, an oil or combinations thereof, determining the concentration of the additional component and utilizing a separation technique to remove at least a portion of the additional component from the commercial fragrance formulation to form a composition wherein the portion of the additional component is from about 5 wt. % to about 95 wt. % of the commercial fragrance formulation. The method further includes adding an additional fragrance component to the composition to form a new formulation, wherein the additional fragrance component is added to the composition in an amount substantially equal to the portion of the additional component removed from the commercial fragrance formulation.

Embodiments of the invention can further include a method of forming a clear fragrance. The method further includes preparing a solution from the new formulation and processing the solution to form a clear fragrance, wherein the processing comprises mixing, heating to a temperature of from about 20° C. to about 68° C. or combinations thereof. The clear fragrance is adapted to enhance solubility, enhance functional compatibility, enhance performance, reduce sweating, or combinations thereof, of the clear fragrance when added to an article.

BRIEF DESCRIPTION OF THE DRAWINGS

Aspects of the present invention will be described in greater detail with reference to the appended figures.

DETAILED DESCRIPTION

Figure 1:
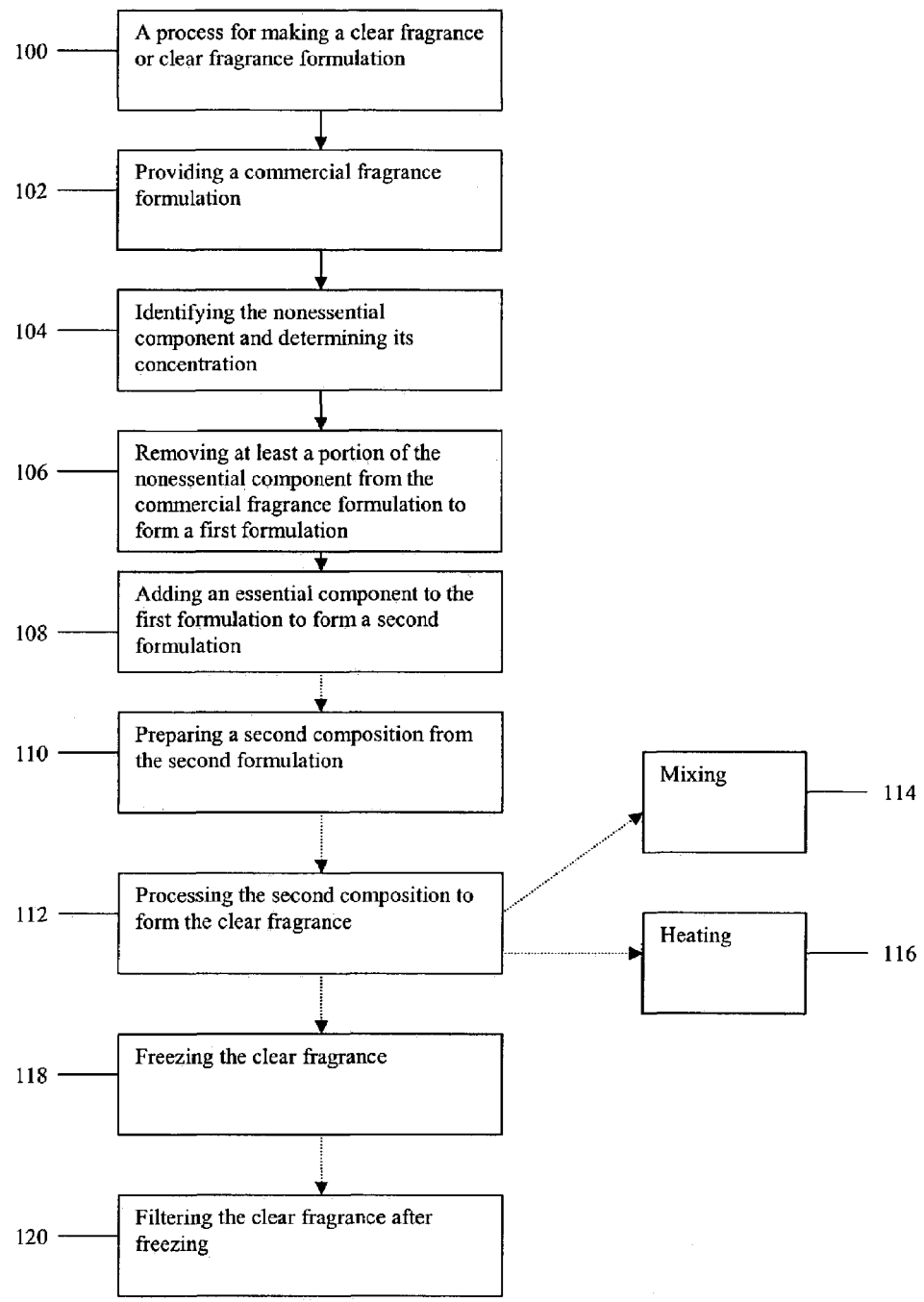
FIG. 1 illustrates a flow diagram of an embodiment of the invention.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the pertinent art to make and use the inventions, when the information in this patent is combined with available information and technology. Various terms as used herein are defined below. To the extent a term used in a claim is not defined below, it should be given the broadest definition persons in the pertinent art have given that term as reflected in printed publications and issued patents.

Embodiments of the invention generally include a method of forming a clear fragrance or a clear fragrance formulation 100. FIG. 1 illustrates a flow diagram of embodiments described herein.

The method generally includes providing a commercial fragrance formulation 102, the commercial fragrance formulation including a first concentration of a fragrance component and a second concentration of an additional component. A commercial fragrance formulation useable to the processes described herein can include any commercially available fragrance, such as Bayberry Fragrance Oil formulation No. FG0268, Vanilla Fragrance Oil formulation No. FG0258, Rain Fragrance Oil formulation No. FG0126 and Cherry Fragrance Oil formulation No. FG0244, which are commercially available form Intercontinental Fragrances, L.L.C. of Houston, Tex. Further, over 10,000 additional commercial fragrances are available from Intercontinental Fragrances, L.L.C.

As used herein, the term "fragrance" refers to one or more compounds having an odor and which is known to one skilled in the art as being useful as a perfuming ingredient or to effectively mask the natural odor of other ingredients in the household article or in the air to enhance acceptance by the user.

The additional components can include a variety of components/ingredients which are not necessary to enhance a property, such as odor, diffusion, or solubility, of the commercial fragrance. In an embodiment, the additional component can be odorless. Further, the additional components can include a variety of compounds, such as those listed below.

The additional component can include an alcohol, such as benzyl alcohol, phenyl ethyl alcohol, cinnamic alcohol, glycol or other similar alcohols possessing the properties/functionalities of the additional component described herein. Although described herein in terms of an additional component including an alcohol, an ester, a hydrocarbon, an aldehyde, a resin, another crystalline aroma chemical or an essential oil, any number of additional components having any number of compounds described herein can be used. In one embodiment, the additional component includes from about 5 wt. % to about 50 wt. % alcohol.

The additional component can include an ester, such as phthalate ester, abietic ester, palmitic ester, myristic ester, adipic ester, stearic ester, oleic ester, ethyl acetate, methyl salicylate or any other ester possessing the properties/functionalities of the additional component described herein.

The additional component can include a hydrocarbon, such as a terpenic hydrocarbon, an aromatic hydrocarbon, an aliphatic hydrocarbon or any other hydrocarbon possessing the properties/functionalities of the additional component described herein. The terpenic hydrocarbon can be pinene, limonene, dipentene, camphene, myrcene, cymene, ocimene, a sesquiterpenic hydrocarbon, or phellandrene, for example. The sesquiterpenic hydrocarbon can include caryophyllene or bisabolene, for example.

The additional component can include an aldehyde, such as cinnamic aldehyde, citral, acetaldehyde, cumin aldehyde or any other aldehyde possessing the properties/functionalities of the additional component described herein.

The additional component can include a resin, such as balsam peru resin, olibanum resin, opoponax resin, elemi resin or any other resin possessing the properties/functionalities of the additional component described herein.

The additional component can include crystalline aroma chemical, such as vanillin, coumarin, heliotropin or any other crystalline aroma chemical possessing the properties/functionalities of the additional component described herein.

The additional component can include an oil, such as orange oil, lemon oil, pine oil, eucalyptus oil, calamus oil, costus oil, cade oil, lime oil, citronella oil, peppermint oils, opoponax oil, styrax oil, vegetable oils, or any other oil possessing the properties/functionalities of the additional component described herein.

The method further includes identifying the additional component and determining the second concentration 104. Identification can be performed by any process known to one skilled in the art.

The method then includes removing at least a portion of the additional component from the commercial fragrance formulation to form a first formulation 106. As known to one skilled in the art, the amount of the portion of the additional component removed depends on the concentration and components of an article to which the clear fragrance will be added. Preferably, the portion of the additional component is from about 5 wt. % to about 95 wt. % of the commercial fragrance formulation. In an embodiments, the portion of the additional component is from about 30 wt. % to about 70 wt. % of the commercial fragrance formulation. Any separation technique can be used to remove the portion of the additional component from the commercial fragrance formulation.

When the commercial fragrance formulation includes more than one additional component, any combination of the additional components can be removed in independently selected proportions.

For example, a portion of cinnamic aldehyde can be removed from the commercial fragrance formulation, because it may interfere with subsequent processing of a clear fragrance produced from the clear fragrance formulation, e.g., when present in concentrations of greater than 30 wt. %, the cinnamic aldehyde may not be soluble in paraffin, such as a candle. Therefore, it is desirable to remove a portion of cinnamic aldehyde and replace it with an equivalent amount of an additional fragrance component to improve solubility of the clear fragrance in paraffin.

Next, the method includes adding an additional fragrance component to the first formulation to form a second formulation 108. Preferably, the additional fragrance component is added to the first formulation in an amount substantially equal to the portion of the additional component removed from the commercial fragrance formulation.

The additional fragrance component can include a variety of ingredients which enhance the performance of the fragrance component. For example, at least one of the additional fragrance components can be adapted to contribute to a functional compatibility of a clear fragrance with a desired product, such as candles, soaps, laundry detergent, air fresheners and other household products. Further, the additional fragrance components can include a variety of compounds, such as those listed below.

The additional fragrance component can include an alcohol, such as anisic alcohol, phenyl ethyl alcohol, geraniol, or any other alcohol possessing the properties/functionalities of the additional fragrance component described herein. Although described herein in terms of an additional fragrance component including an alcohol, an ester, an aldehyde, a phenol, an acetal, a ketone, a pyrazinc, a thiozole, an essential oil, or an organic acid, any number of additional fragrance components having any number of compounds described herein can be used.

The additional fragrance component can include an ester, such as benzyl propionate, styrallyl acetate, isobornyl propionate, citronelly formate or any other ester possessing the properties/functionalities of the additional fragrance component described herein.

The additional fragrance component can include an aldehyde, such as phenyl acetic aldehyde, cuminic aldehyde, anisic aldehyde, hydrotropic aldehyde, or any other aldehyde possessing the properties/functionalities of the additional fragrance component described herein.

The additional fragrance component can include a phenol, such as paracresol, orthocresol, eugenol, or any other phenol possessing the properties/functionalities of the additional fragrance component described herein.

The additional fragrance component can include an acetal, such as phenyl acetaldehyde dimethyl acetal, hydrotropic aldehyde dimethyl acetal, or any other acetal possessing the properties/functionalities of the additional fragrance component described herein.

The additional fragrance component can include a ketone, such as methyl naphthyl ketone, raspberry ketone, or any other ketone possessing the properties/functionalities of the additional fragrance component described herein.

The additional fragrance component can include a pyrazine, such as 2,5-dimethyl pyrazine, 2,6-dimethyl pyrazine, diethyl methyl pyrazine, or any other pyrazine possessing the properties/functionalities of the additional fragrance component described herein.

The additional fragrance component can include a thiazole, such as 2,4-dimethyl thiazole, isopropyl-4-methyl thiazole, or any other thiazole possessing the properties/functionalities of the additional fragrance component described herein.

The additional fragrance component can include an essential oil, such as lavender oil, bergamot oil, rose oil, jasmine oil, or any other essential oil possessing the properties/functionalities of the additional fragrance component described herein.

The additional fragrance component can include an organic acid, such as lactic acid, butyric acid, caproic acid, or any other acid possessing the properties/functionalities of the additional fragrance component described herein.

Embodiments of the invention can further include a method of forming a clear fragrance. These methods include those enumerated above, in addition to further steps described in greater detail below.

For example, the method can include preparing a second composition from the second formulation 110 and processing the second component to form the clear fragrance 112.

The clear fragrance is preferably concentrated. Further, the clear fragrance can be a homogenous dispersion.

The processing can include any process which enhances dispersion in the second component. For example, the processing can include mixing 114 and/or heating 116 to a temperature of from about 20° C. to about 68° C. In one embodiment, the process includes heating the second composition to a temperature of from about 25° C. to about 65° C. to compensate for a loss of endothermic energy during the processing of the second composition.

Additional steps of the method can include freezing 118 the clear fragrance to a temperature of at least −5° C. to prevent recrystallization in the clear fragrance at ambient temperatures.

Further, the method can include filtering 120 the clear fragrance after freezing 118 to stabilize the clear fragrance. Stabilization can be useful in situations where the second composition reaches maximum saturation.

The embodiments described herein generally result in a clear fragrance that is concentrated versus conventional fragrances. As a result, a smaller amount of the fragrance can be used in commercial and household products with the same effect as conventional fragrances. Further, the clear fragrances described herein are generally adapted to be compatible with ingredients in commercial products so as to not over-saturate the product when combined. Preferably, the clear fragrance is adapted to enhance solubility, enhance functional compatibility, enhance performance or reduce sweating, for example, of the clear fragrance when added to an article, such as a household or consumer article. For example, when used to form paraffin based objects, the embodiments described herein generally reduce or eliminate sweating of the candle, provide better burning properties to the candle and result in less sooting of the candle.

Hypothetical Example

A clear fragrance will be prepared by using a commercial fragrance Cinnamon Fragrance Oil formula No. FG0254 having the following formula:

| Compound | wt. % |
| --- | --- |
| Cinnamon leaf essential oil | 1 |
| Coumarin crystalline aroma chemical | 2 |
| Vanillin | 2 |
| Cinnamic alcohol | 5 |
| Benzyl acetate | 8 |
| Orange oil terpene | 20 |
| Rosin ester | 20 |
| Cinnamic Aldehyde | 42 |

15 wt. % rosin esters and 26 wt. % cinnamic aldehyde can then be removed from the commercial fragrance formulation to form a first formulation.

21 wt. % eugenol, 10 wt. % cinnamon leaf oil, 5 wt. % benzyl acetate, 1 wt. % benzaldehyde and 4 wt. % methoxy cinnamic aldehyde will be added to the first formulation to form a second formulation.

A second component will then be formed from the second formulation. The second composition will then be mixed and heated to form the clear fragrance at a temperature of about 46 C for a time of about 10 minutes.

It is believed that the clear fragrance will be a homogenous, translucent dispersion of essential components.

While the foregoing is directed to the preferred embodiments of the present invention, other and further embodiments of the invention can be devised without departing from the basic scope thereof, and the scope thereof is determined by the claims that follow.

What is claimed is:

1. A method for making a clear fragrance comprising:
   a. providing a commercial fragrance formulation comprising a fragrance component and an additional component;
   b. identifying the additional component, wherein the additional component comprises an alcohol, an ester, a hydrocarbon, an aldehyde, a resin, an oil, or combinations thereof;
   c. determining the concentration of the additional component from the commercial fragrance formulation;
   d. utilizing a separation technique to remove at least a portion of the additional component from the commercial fragrance formulation to form a composition, wherein at least a portion of the additional component comprises from about 5 wt. % to about 95 wt. % of the commercial fragrance formulation;
   e. adding an additional fragrance component selected from the group consisting of: an additional alcohol different from the removed alcohol, an additional ester different from the removed ester, an additional aldehyde, a phenol, an acetal, a ketone, a pyrazine, a thiazole, an essential oil different from the removed oil, and an organic acid, to the composition to form a new formulation, wherein the additional fragrance component is added to the composition in an amount substantially equal to the portion of the additional component removed from the commercial fragrance formulation;
   f. preparing a solution from the new formulation; and
   g. processing the solution to form a clear fragrance, wherein the processing is selected from a member of the group consisting of: mixing and heating to a temperature of from about 20° C. to about 68° C.

2. The method of claim 1, wherein the ester comprises phthalate ester, abietic ester, palmitic ester, myristic ester, adipic ester, stearic ester, oleic ester, ethyl acetate, methyl salicylate, or combinations thereof.

3. The method of claim 1, wherein the alcohol comprises benzyl alcohol, phenyl ethyl alcohol, cinnamic alcohol, glycol, or combinations thereof.

4. The method of claim 1, wherein the commercial fragrance formulation comprises from about 5 wt. % to about 50 wt. % alcohol.

5. The method of claim 1, wherein the hydrocarbon comprises a terpenic hydrocarbon, an aromatic hydrocarbon, an aliphatic hydrocarbon or combinations thereof.

6. The method of claim 5, wherein the terpenic hydrocarbon comprises pinene, limonene, dipentene, camphene, myrcene, cymene, ocimene, a sesquiterpenic hydrocarbon, phellandrene or combinations thereof.

7. The method of claim 6, wherein the sesquiterpenic hydrocarbon comprises caryophyllene, bisabolene or combinations thereof.

8. The method of claim 1, wherein the aldehyde comprises cinnamic aldehyde, citral, acetaldehyde, cumin aldehyde, or combinations thereof.

9. The method of claim 1, wherein the oil comprises orange oil, lemon oil, pine oil, eucalyptus oil, calamus oil, costus oil, cade oil, lime oil, citronella oil, peppermint oil, opoponax oil, styrax oil, vegetable oil, or combinations thereof.

10. The method of claim 1, wherein the resin comprises balsam peru resin, olibanum resin, opoponax resin, elemi resin or combinations thereof.

11. The method of claim 1, wherein the additional component is odorless.

12. The method of claim 1, wherein the at least a portion of the additional component comprises from about 30 wt. % to about 70 wt. % of the commercial fragrance formulation.

13. The method of claim 1, wherein the heating comprises heating the solution to a temperature of from about 25° C. to about 65° C.

14. The method of claim 1, wherein the clear fragrance is a homogenous dispersion.

15. The method of claim 1, wherein further comprising freezing the clear fragrance to a temperature of at least −5° C. to prevent recrystallization of the clear fragrance at ambient temperatures.

16. The method of claim 15, wherein further comprising filtering the clear fragrance after freezing to stabilize the clear fragrance.

17. The method of claim 1, wherein the fragrance component is a member of the group consisting of: an alcohol, an ester, an aldehyde, a phenol, an acetal, a ketone, a pyrazine, a thiazole, an oil, an organic acid, or combinations thereof.

18. The method of claim 1, wherein the clear fragrance is a concentrate.

19. The method of claim 17, wherein the alcohol comprises anisic alcohol, phenyl ethyl alcohol, geraniol, or combinations thereof.

20. The method of claim 17, wherein the ester comprises benzyl propionate, styrallyl acetate, isobornyl propionate, citronellyl formate, or combinations thereof.

21. The method of claim 17, wherein the aldehyde comprises phenyl acetic aldehyde, cuminic aldehyde, anisic aldehyde, hydrotropic aldehyde, or combinations thereof.

22. The method of claim 17, wherein the phenol comprises paracresol, orthocresol, eugenol, or combinations thereof.

23. The method of claim 17, wherein the acetal comprises phenyl acetaldehyde dimethyl acetal, hydrotropic aldehyde dimethyl acetal, or combinations thereof.

24. The method of claim 17, wherein the ketone comprises methyl naphthyl ketone, raspberry ketone, or combinations thereof.

25. The method of claim 17, wherein the pyrazine comprises 2,5-dimethyl pyrazine, 2,6-dimethyl pyrazine, diethyl methyl pyrazine, or combinations thereof.

26. The method of claim 17, wherein the thiazole comprises 2,4-dimethyl thioazole, isopropyl-4-methyl thiazole, or combinations thereof.

27. The method of claim 17, wherein the oil comprises lavender oil, bergamot oil, rose oil, jasmine oil, or combinations thereof.

28. The method of claim 17, wherein the organic acid comprises lactic acid, butyric acid, caproic acid, or combinations thereof.

29. A method for forming a clear fragrance comprising:

a. providing a commercial fragrance formulation comprising a fragrance component and an additional component;

b. identifying the additional component, wherein the additional component comprises an alcohol, an ester, a hydrocarbon, an aldehyde, a resin, an oil or combinations thereof;

c. determining the concentration of the additional component from the commercial fragrance formulation;

d. utilizing a separation technique to remove at least a portion of the additional component from the commercial fragrance formulation to form a composition, wherein at least a portion of the additional component is different from the removed additional component and comprises from about 5 wt. % to about 95 wt. % of the commercial fragrance formulation; and e. adding an additional fragrance of component to the composition to form a clear fragrance, wherein the additional fragrance component is added to the composition in an amount substantially equal to the portion of the additional component removed from the commercial fragrance.

* * * * *